United States Patent

Marnett et al.

Patent Number: 5,234,933
Date of Patent: Aug. 10, 1993

[54] CYCLIC HYDROXAMIC ACIDS

[75] Inventors: Lawrence J. Marnett, Nashville, Tenn.; Kenneth V. Honn; Carl R. Johnson, both of Detroit, Mich.; Yung-fa Chen, Tainan, Taiwan; Katsu-ichi Shimoji, Detroit, Mich.

[73] Assignee: Board of Governors of Wayne State University and Vanderbilt University, Nashville, Tenn.

[21] Appl. No.: 785,927

[22] Filed: Oct. 31, 1991

[51] Int. Cl.$^5$ .................. C07D 211/40; A61K 31/445
[52] U.S. Cl. ...................... 514/327; 514/319; 546/205; 546/216; 546/206
[58] Field of Search ............... 546/206, 205, 221, 216; 514/330, 319, 327

[56]  References Cited
U.S. PATENT DOCUMENTS
4,322,440 3/1982 Fish et al. ..................... 514/563

FOREIGN PATENT DOCUMENTS
WO91/16303 10/1991 World Int. Prop. O. .

OTHER PUBLICATIONS
Aurich et al "Aminyl oxides" CA 80:59341s (1974).
Societa Farmacentici Italia "N-hydroxylactams" CA 61:3075g (1964).
Panizzi et al. "Action of nitroxyl on ketonic comp." CA 57:9659a (1961).

Primary Examiner—C. Warren Ivy
Assistant Examiner—Celia Chang
Attorney, Agent, or Firm—Ian C. McLeod

[57]  ABSTRACT

Novel cyclic hydroxamic acids of the general formula:

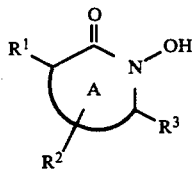

(I)

wherein ring A is 5- or 6-membered;
$R^1$, $R^2$ and $R^3$ each, independently, is hydrogen, C1-24 alkyl, C2-24 alkenyl or a group of the formula:

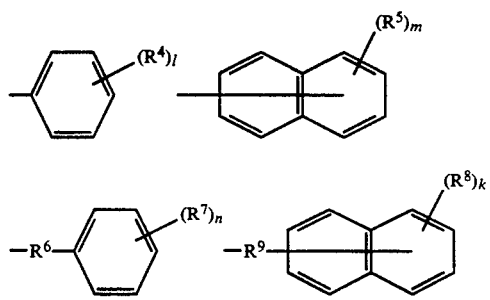

wherein $R^4$, $R^5$, $R^7$ and $R^8$ each, independently is hydrogen,
C1-4 alkyl, C1-4 alkoxy, trifluoromethyl, halogen or nitro; l is 1-3; m is 1-3; n is 1-3; k is 1-3;
$R^6$ and $R^9$ each, independently is C1-24 alkylene or C2-24 alkenylene;

With the proviso that, more than one of $R^1$, $R^2$ and $R^3$ are not hydrogen at the same time; and the pharmaceutically acceptable salts thereof possesses an inhibitory activity against 12-lipoxygenase, and therefore, may be useful for treating and/or preventing inflammation, immune diseases, psoriasis, arteriosclerosis and/or ischaemic cardiovascular diseases and also for suppressing metastasis of cancer.

9 Claims, No Drawings

CYCLIC HYDROXAMIC ACIDS

SUMMARY

This invention relates to novel compounds having an inhibitory activity against 12-lipoxygenase.

More particularly, this invention is related to 1) novel cyclic hydroxamic acids having an inhibitory activity against 12-lipoxygenase, of the following general formula:

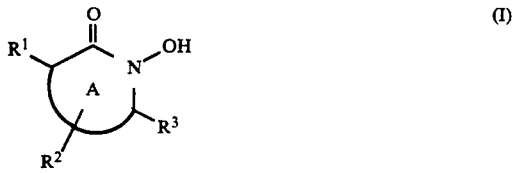

(I)

and the pharmaceutically acceptable salts thereof and 2) process for the preparation of them, and 3) 12-lipoxygenase inhibiting agents containing them as an active ingredient.

BACKGROUND OF THE INVENTION

Lipoxygenases are the enzymes related to the oxydative metabolic pathway of unsaturated fatty acids. 5-, 8-, 11-, 12- and 15-lipoxygenases are rather well characterized enzymes among those enzymes. A particular lipoxygenase oxidizes a particular position of arachidonic acid to produce a particular metabolite. For example, 5(S)-lipoxygenase produces 5-HETE ((5(S)-5-hydroxyeicosa-6(E),8(Z),11(Z),14(Z)-tetraenoic acid or LTs (so called leukotrienes) through 5-HPETE (5(S)-5-hydroperoxyeicosa-6(E),8(Z),11(Z),14(Z)-tetraenoic acid).

In spite of being found in mammalian tissue the role of 12-lipoxygenase is not well known.

12(S)-HETE (12(S)-hydroxyeicosa-5(Z),8(Z),10(E), 14(Z)-tetraenoic acid), a metabolite of arachidonate, is produced by 12-lipoxygenase and possesses a variety of biological characteristics, e.g., an antagonism of LTB4 and an enhancement of the enzyme activity of 5-lipoxygenase. It is thought that 12-lipoxygenase is involved in inflammation and immunity. Further, it is also thought that lipoxygenases are closely related to ischemic heart diseases and ischemic brain diseases.

It has been reported that 12-HETE induces a chemotactic reaction of smooth muscle cells in rat (Atherosclerosis, 44, 339, 1982). It was thought that such chemotactic action of 12(S)-HETE produced by 12-lipoxygenase in plasma platelets might be related to the induction of arteriosclerosis.

Recent studies have shown that some types of cancer cells can induce aggregation of plasma platelets. Cancer cells activate plasma platelets, in such a way that metabolites of arachidonate are released. Among these metabolites, a considerable amount of 12-HETE was detected (Cancer Res., 47, 6751, 1987; ibid 47, 25, 1987).

It has been also found that a process of cancer metastasis involves adhesion of a cancer cell(s) to subendothelial matrices through receptors, the expression of which expression is enhanced by 12-HETE (Cancer Res., 49, 1029, 1989).

A 12-lipoyxgenase inhibitor inhibits the production of 12-HETE by 12-lipoxygenase. Therefore, 12-lipoxygenase inhibitor may be useful for the treatment and/or prevention of inflammation, cancer metastasis, immune diseases, psoriasis, arteriosclerosis and/or ischaemic cardiovascular diseases.

RELATED ARTS

Certain types of chemicals are known to be 12-lipoxygenase inhibitors, and, among these are hydroxamic acid derivatives.

For example, these compounds are disclosed in the specification of

1. Derwent No. 89-295760,
2. European Patent Publication No. 320,628,
3. ibid 320,000,
4. ibid 388,429,
5. ibid 346,939,
6. ibid 279,281,
7. ibid 279,263,
8. U.S. Pat. No. 4,822,809

In these related arts, for example, European Patent Publication No. 320,628 disclosed the compounds of the following general formula:

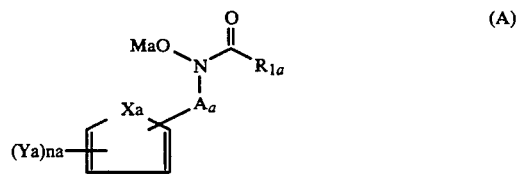

(A)

$R^{1a}$=H, 1-4C alkyl, 2-4C alkenyl or $NR^{2a}R^{3a}$;

$R^{2a}$, $R^{3a}$=H, 1-4C alkyl, OH or aryl (optionally substituted by halo, $NO_2$, CN, 1-12C alkyl, alkoxy, haloalkyl, alkoxycarbonyl, $CONH_2$, mono- or di-alkylaminocarbonyl or alkylsulphonyl;

provided that $R^{2a}$ and $R^{3a}$ are not both OH;

Xa=0 or $NR^{4a}$;

$R^{4a}$=H, 1-6C alkyl, 1-6C alkoyl, aralkyl or aroyl;

Aa=1-6C alkylene or 2-6C alkenylene;

na=0–3;

each Ya=H; halo; OH; CN; haloalkyl; 1-12C alkyl; 2-12C alkenyl; 1-12C alkoxy; 3-8C cycloalkyl; alkoxycarbonyl; aralkoxycarbonyl; $CONH_2$; mono- or di-alkylamino carbonyl; arylalkylamino; arylalkylaminocarbonyl; alkoxyalkoxyalkyl; alkoxyalkyl; or aryl, aryloxy, aroyl, 1-12C aralkyl, 2-12C aralkenyl, 1-12C aralkoxy, 1-12C arylthioalkoxy, arylalkoxyalkyl or arylthioalkoxyalkyl, optionally substituted by halo, $NO_2$, CN, 1-12C alkyl, alkoxy or haloalkyl;

Ma=H, pharmaceutically acceptable cation, aroyl or 1-12C alkoyl;

provided that when Ma, Ya and $R^{1a}$ are H, na=1 and Aa=$CH_2$ then Xa is not 0.

Certain types of cyclic hydroxamic acid derivatives also are known to be lipoxygenase inhibitors. For example, one of them is disclosed in European Patent Publication No. 196,184 (i.e. Japanese Patent Publication No. 61-257951).

In this specification, the following compounds of the general formula (B) are disclosed as lipoxygenase and cyclooxygenase inhibitor. That is: aryl substituted hydroxamic acid and N-hydroxy lactam compounds of formula:

Arb—(La—Ar'b)qb—(Xb)kb—(Yb)pb—Qb    (B)

kb, pb and qb=0 or 1, provided that when kb=1 then pb=1; Arb=
 (i) naphthyl, tetrahydronaphthyl or pyridyl all optionally substituted by one or more of 1–4C alkyl, haloalkyl or alkoxy, halogen, NO2, NH2, carboxy, (1–4C alkoxy)carbonyl or OH, or
 (ii) phenyl, optionally substituted as in (i) or by phenyl itself optionally substituted as in (i);
Lb=—(CH2)rb—(rb=1–4), —O—, —CH2O—, —CH2S—, —OCH2—, —CONH—, —NHCO—, —CO— or —CH2NH—;
Ar'b=phenylene, thienylene or pyridylene, all optionally substituted, as in (i);
 Xb=O, S or CO, provided that at least 1 atom separates CO from any CO group in Qb (below);
 Yb=1–10C alkylene or alkenylene;
 Qb=1-hydroxy-1,3-dihydro-imidazol-2-one or a group of formula (IIb) or (IIIb);

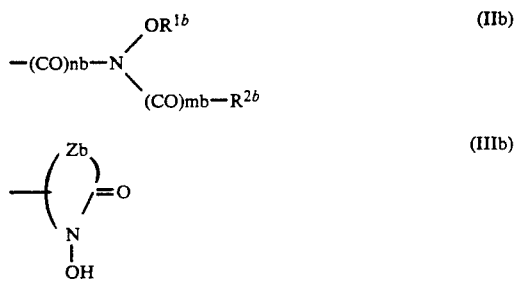

mb=0 and nb=1 or mb=1 and nb=0;
 when nb=1: R$^{1b}$ and R$^{2b}$=H or 1–4C alkyl, or R$^{2b}$ may also be 5–7C cycloalkyl;
 when mb=1: R$^{1b}$=H, 1–4C alkyl, COR$^{3b}$ or a value of Arb, and R$^{2b}$=H, 1–4C alkyl, NH2, 1–4C alkylamino, di(1–4C alkyl)amino, 5–7C cycloalkylamino, 5–7C cycloalkyl(1–4C alkyl)amino, anilino, N-1–4C alkylanilino or a value of Arb;
 R$^{3b}$=1–4C alkyl (optionally substituted by carboxy or (1–4C alkoxycarbonyl) or —NR$^{4b}$R$^{5b}$;
 R$^{4b}$=H or 1–4C alkyl;
 R$^{5b}$=H, 1–4C alkyl or phenyl optionally substituted by substituent(s) as in (i); and
 Zb=2–5C alkylene in which a C atom may be replaced by a heteroatom.
provided that when qb=O, kb=O or lb and pb=1, Ab=phenyl or naphthyl (both optionally substituted as in (i) and Xb=O or S (when k=1), Yb=alkylene and Qb=(II) in which R$^{1b}$ or R$^{2b}$=H or 1–4C alkyl, then the other of R$^{1b}$ and R$^{2b}$ is neither H nor 1–4C alkyl.

In this specification, for example, compounds of formula:

71)
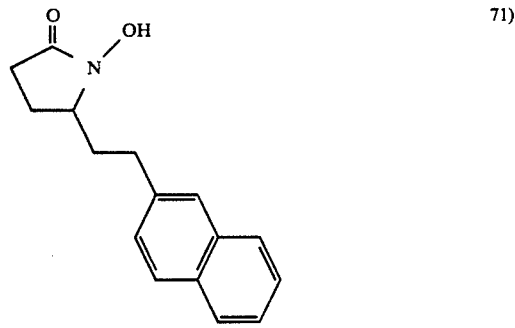

73)
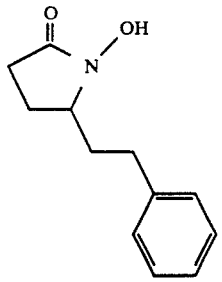

are concretely disclosed in example 71 and 73.

The inhibitory activity was measured against 5-lipoxygenase in laboratory tests.

In comparison to the above compounds, the compounds of the present invention are structurally different in the following point: the compounds of the present invention always have at least two substituents on the carbons of the pyrrolidinone or piperidinone rings.

Further, the compounds of the present invention of the general formula (I) inhibit strongly 12-lipoxygenase.

Since, there are no descriptions that include or indicate the compounds of the present invention in the earlier disclosures, the compounds of the present invention, therefore, are novel and unobvious.

DISCLOSURE OF THE INVENTION

We, the present inventors, have synthesized cyclic hydroxamic acids, and find the compounds possess an inhibitory activity against 12-lipoxygenase. The compounds of the present invention which suppress the production of 12-HETE by 12-lipoxygenase will be useful for the treating and/or preventing of inflammation, immune diseases, psoriasis, arteriosclerosis and/or ischaemic cardiovascular diseases and also act as suppressing agents of metastasis of cancer.

DISCLOSURE OF THE INVENTION

The present invention is related to
1) Novel cyclic hydroxamic acids of the formula:

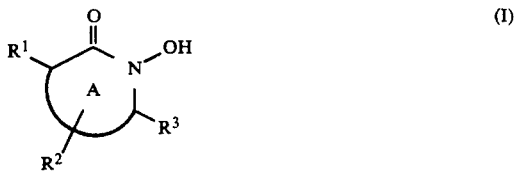
(I)

wherein ring A is 5- or 6-membered;
 R$^1$, R$^2$ and R$^3$ each, independently, is hydrogen, C1-24 alkyl, C2-24 alkenyl or a group of the formula:

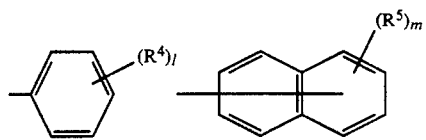

-continued

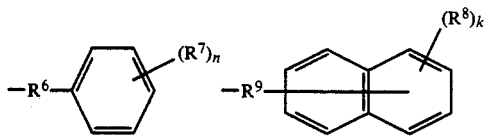

wherein $R^4$, $R^5$, $R^7$ and $R^8$ each, independently, is hydrogen, C1-4 alkyl, C1-4 alkoxy, trifluoromethyl, halogen or nitro;
l is 1-3;
m is 1-3;
n is 1-3;
k is 1-3;
$R^6$ and $R^9$ each, independently, is C1-24 alkylene or C2-24 alkenylene;
With the proviso that, more than one of $R^1$, $R^2$ and $R^3$ are not hydrogen at the same time;
and pharmaceutically acceptable salts thereof and
2) process for the preparation of the above compounds and
3) 12-lipoxygenase inhibiting agents containing them as active ingredient.

In the general formula (I), ring A means pyrrolidine and piperidine ring.

In the general formula (I), C1-24 alkyl in $R^1$, $R^2$ and $R^3$ means methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl and isomeric groups thereof.

In the general formula (I), C2-24 alkenyl in $R^1$, $R^2$ and $R^3$ means groups wherein one, two, three or four double bonds are induced to the above alkyl groups.

In the general formula (I), C1-24 alkylene in $R^6$ and $R^9$ means methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, heptadecamethylene, octadecamethylene, nonadecamethylene, eicosamethylene, heneicosamethylene, docosamethylene, tricosamethylene, tetracosamethylene and isomeric groups thereof.

In the general formula (I), C2-24 alkenylene in $R^6$ and $R^9$ means group wherein one, two, three or four double bonds are induced to the above alkylene groups.

In the general formula (I), halogen in $R^4$, $R^5$, $R^7$ and $R^8$ means chlorine, bromine, fluorine and iodine atoms.

In the general formula (I), C1-4 alkyl in $R^4$, $R^5$, $R^7$ and $R^8$ means methyl, ethyl, propyl, butyl and isomeric groups thereof.

In the general formula (I), C1-4 alkoxy in $R^4$, $R^5$, $R^7$ and $R^8$ means methoxy, ethoxy, propyloxy and butyloxy and isomeric groups thereof.

For example, it may be easily understood that alkyl, alkoxy, alkenyl, alkylene and alkenylene groups include straight-chained and also branched-chained ones, to those skilled in the art.

In the general formula (I), any singly bonded substituent may be attached to up or down relative to the ring plane.

Salts

The compounds of the formula (I) may be converted into the corresponding salts. Non-toxic and water-soluble salts are preferable. Suitable salts, for example, are as follows: salts of alkaline metal (sodium, potassium etc.), salts of alkaline earth metal (calcium, magnesium etc.) ammonium salts, salts of pharmaceutically acceptable organic amine (tetramethylammonium, trimethylamine, dimethylamine, cyclopentylamine, benzylamine, phenethylamine, piperidine, monoetanolamine, diethanolamine, tris(hydroxymethyl)amine, lysine, arginine, N-methyl-D-glucamine etc.)

The compounds of the formula (I) or salts thereof may be in a form of hydrate.

PROCESSES FOR PREPARATIONS

Compounds of the general formula (I) may be prepared by cyclization of a compound of general formula:

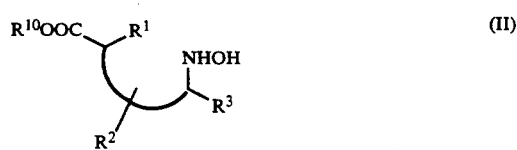

wherein

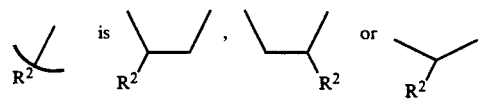

and $R^{10}$ is hydrogen or C1-4 alkyl and the other symbols are as described before.

Cyclization was known reaction, and it may be carried out, for example, by reacting a compound of the general formula (II), in the presence or the absence of silica, in an inert organic solvent (e.g., benzene, toluene, xylene) with refluxing.

PROCESS FOR THE PREPARATION OF THE INTERMEDIATES

Intermediates of the compounds of the present invention of the formula (II) may be prepared by a series of known reaction process described in the following reaction scheme (A).

Each symbol in the scheme(s) is as described hereinbefore, respectively.

Scheme (A)

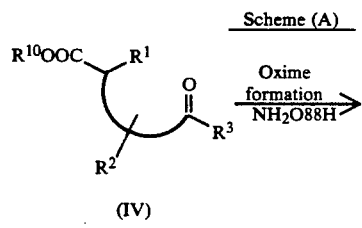

(IV)

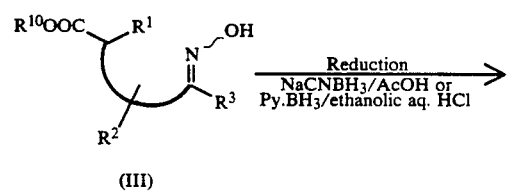

(III)

-continued
Scheme (A)

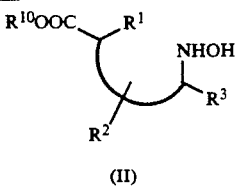

(II)

In each reaction in the present specification, products may be purified by conventional means, for example, by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

Starting materials and reagents in the present invention are known per se or may be prepared by known methods.

Pharmacological Activity

The compounds of the present invention of the general formula (I) possess an inhibitory activity on 12-lipoxygenase, described before, for example, in standard laboratory test, the results in the Table I were found.

TABLE I

| $IC_{50}$ for 12-Lipoxygenase | |
|---|---|
| Example No. of the compounds | $IC_{50}$ ($\mu M$) |
| 1 | 0.42 |
| 1(a) | 0.15 |
| 1(j) | 0.28 |
| 1(k) | 0.39 |
| 1(o) | 0.13 |
| 1(q) | 0.1 |
| 1(v) | 0.7 |
| 1(w) | 0.8 |

The standard assay procedure is as follows:

Compounds of the present invention were added in 3 $\mu L$ of DMSO at an appropriate concentration to porcine leukocyte cytosol in buffer (final protein concentration of 0.075 mg/mL in 0.1M HEPES, 2 mM $CaCl_2$, 1 mM $MgCl_2$, pH=8.0) and preincubated for 5 min at 37° C. [$1-^{14}C$]arachidonic acid was added (final concentration of 5 $\mu M$) and the reactions were incubated for 15 min at 37° C. and terminated by the addition of HCl. Total reaction volume was 100 $\mu L$. Assays also included reduced glutathione in the assay at 25 $\mu M$ or following the assay at 1 mM and/or cold carrier 12-HETE and arachidonic acid added at the end of the incubation at concentrations of 5 and 100 $\mu M$, respectively. Sample was extracted with water-saturated ethyl acetate and the extracts were spotted onto TLC plates. The plates were developed with dichloromethane/ethyl acetate/acetic acid in a ratio of 70:30:1. Under these conditions, the Rf's of 12-HETE and arachidonic acid are 0.30 and 0.45, respectively. The percentage conversion to 12-HETE was calculated from the percentage of the total $^{14}C$ on the TLC plate that coelutes with a standard of 12-HETE.

Toxicity

Toxicities of the compounds of the present invention were very low, and are therefore, estimated to be safe for pharmaceutical use.

Applications for Pharmaceuticals

Inhibition of 12-lipoxygenase to suppress the production of 12-HETE may be useful for prevention and/or treatment of inflammation, immune diseases, psoriasis, arteriosclerosis and/or ischaemic cardiovascular diseases and also suppressing metastasis of cancer in animals including humans.

Since the compounds of the present invention possess an inhibitory activity against 12-lipoxygenase in vitro, it is expected to be useful for prevention and/or treatment of the above diseases.

For the purposes described above, the compounds of the present invention may normally be administered systemically of partially, usually by oral or parenteral administration.

The doses to be administered are determined depending upon age, body weight, symptom, the desired therapeutic effect, the route of administration, and the duration of the treatment etc. In a human adult, the doses per person per administration are generally between 1 mg and 500 mg, by oral administration, up to several times per day, and between 1 mg and 100 mg, by parenteral administration up to several times per day.

Since, the doses to be used depend upon various conditions, as mentioned above, there may be a case in which doses are lower than or greater than the ranges specified above.

Solid compositions for oral administration include compressed tablets, pills, dispersible powders, capsules, and granules. In such compositions, one or more of the active compound(s) is or are, admixed with at least one inert diluent (lactose, mannitol, glucose, hydroxypropylcellulose, microcrystalline cellulose, starch, polyvinylpyrrolidone, magnesium metasilicate alminate etc.). The compositions may also comprise, as is normal practice, additional substances other than inert diluents: e.g. lubricating agents (magnesium stearate etc.), disintegrating agents (cellulose calcium glycolate etc.), and assisting agent for dissolving (glutamic acid, aspartic acid etc.) stabilizing agent (lactose etc.).

The tablets or pills may, if desired, be coated with gastric or enteric material (sugar, gelatin, hydroxypropylcellulose or hydroxypropylmethyl cellulose phthalate etc.).

Capsules include soft ones and hard ones.

Liquid compositions for oral administration include pharmaceutically-acceptable emulsions, solutions, suspensions, syrups and elixirs. In such compositions, one or more of the active compound(s) is or are admixed with inert diluent(s) commonly used in the art (purified water, ethanol etc.). Besides inert diluents, such compositions may also comprise adjuvants (wetting agents, suspending agents etc.), sweetening agents, flavoring agents, perfuming agents and preserving agents.

Other compositions for oral administration include spray compositions which may be prepared by known methods and which comprise one or more of the active compound(s).

Spray compositions may comprise additional substances other than inert diluents: e.g. preserving agents (sodium sulfite etc.), isotonic buffer (sodium chloride, sodium citrate, citric acid etc.).

For preparation of such spray compositions, for example, the method described in the U.S. Pat. No. 2,868,691 or 3,095,355 may be used.

Injections for parenteral administration include sterile aqueous or non-aqueous solution, suspensions and emulsions. In such compositions, one or more of active compound(s) is or are admixed with at least one inert aqueous diluent(s) (distilled water for injection, physiological salt solution etc.) or inert non-aqueous diluent(s) (propylene glycol, polyethylene glycol, olive oil, ethanol, POLYSOLBATE 80 (registered trade mark) etc.).

Injections may comprise additional other than inert diluents: e.g. preserving agents, wetting agents, emulsifying agents, dispersing agents, stabilizing agents (lactose etc.), assisting agents such as for dissolving (glutamic acid, aspartic acid etc.).

They may be sterilized, for example, by filtration through a bacteria-retaining filter, by incorporation of sterilizing agents in the compositions or by irradiation. They also be manufactured in the form of sterile solid compositions, for example, by freeze-drying, and which can be dissolved in sterile water or some other sterile diluents for injection immediately before use.

Other compositions for administration include liquids for external use, and endermic linaments (ointment etc.), suppositories and pessaries which comprise one or more of the active compound(s) and may be prepared by known methods.

REFERENCE EXAMPLES AND EXAMPLES

The following reference examples and examples are illustrative of the present invention, but do not limit the present invention.

The solvents in the parentheses show the developing or eluting solvents and the ratios of the solvents used are by volume in chromatographic separations.

Unless otherwise specified, "NMR spectra" were measured in $CDCl_3$ solution.

Reference Example 1

Preparation of 3-methoxy-5-phenylcyclohex-2-en-1-one

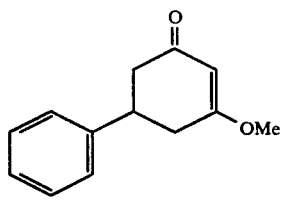

A solution of 3-hydroxy-5-phenylcyclohexane-1,3-dione (14 g) was dissolved in 100 ml of methanol, to which 20 ml of dimethoxypropane and 0.5 g of p-toluenesulfonic acid was added. The resulting mixture was refluxed overnight and was concentrated to ⅓ of its volume. The residue was dissolved in 100 ml of ether and was washed successively with 30 ml each of saturated $NaHCO_3$ and brine. The ether layer was dried over anhydrous $MgSO_4$ and filtered. The filtrate was evaporated to give the title compound (13.5 g) as a light yellow oil.

REFERENCE EXAMPLE 2

Preparation of 3-octyl-5-phenylcyclohex-2-en-1-one

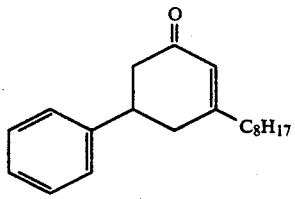

Octylmagnesium bromide (11 ml of 1M THF solution) was added dropwise to a THF (10 ml) solution of the compound prepared in reference example 1 (2.02 g) at 0° C. under argon atmosphere. The reaction mixture was allowed to stand to warm to room temperature in 2 h and stirred at room temperature overnight. After addition of 1 ml of 6N HCl, the reaction mixture was stirred at room temperature for another 30 min. The reaction mixture was diluted with 20 ml of $H_2O$ and extracted with 30 ml of ether. The ether layer was dried over anhydrous $MgSO_4$ and evaporated. The residue was purified by column chromatography on silica gel using a mixture of petroleum ether and EtOAc (10:1) to give the title compound (2.26 g) having the following data:

NMR: $\delta$5.84 (s, 1H), 2.32 (t, 2H), 2.25 (t, 2H), 2.17 (t, 2H), 1.95 (m, 2H), 1.46 (m, 2H) 1.24 (bs, 10H) and 0.85 (t, 3H).

REFERENCE EXAMPLE 3

Preparation of 5-oxo-3-phenyl-tridecanoic acid

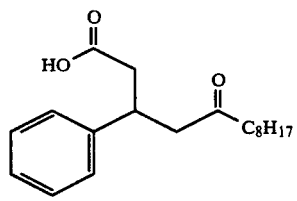

To a solution of the compound prepared in reference example 2 (852 mg) in $CCl_4/CH_3CN$ (20 ml, 1:1) was added an aqueous solution of sodium periodate (2.92 g) and ruthenium oxide hydrate (22 mg). The mixture was stirred at room temperature for 2 h. The resulting solution was extracted three times with 20-ml portions of $CH_2Cl_2$. The combined organic extracts were dried over anhydrous $MgSO_4$. After evaporating, the residue was taken up in 40 ml of ether and filtered through a pad of Fluorosil. The filtrate was evaporated to give the title compound (675 mg) having the following physical data.

NMR: $\delta$11.5 (br, 1H), 7.1–7.3 (m, 5H), 3.68 (m, 1H), 2.78 (d, 2H), 2.68 (dd, 1H), 2.59 (dd, 1H), 2.26 (m, 2H), 1.45 (m, 2H), 1.21 (bs, 10H) and 0.86 (t, 3H).

REFERENCE EXAMPLE 4

Preparation of 5-(N-hydroxyimino)-3-phenyltridecanoic acid

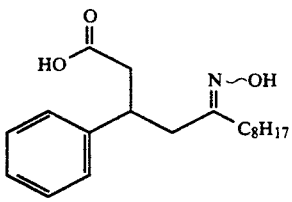

To a solution of the compound prepared in reference example 3 (304 mg) in 5 ml of 95% ethanol was added an aqueous solution of hydroxylamine (165 mg) prepared in situ from 5 equivalent each of hydroxylamine hydrochloride and sodium acetate in 2 ml of $H_2O$. The mixture was stirred at room temperature for 1 h. The resulting solution was diluted with 10 ml of $H_2O$ and extracted with 15 ml of ether. The ether extract was dried over anhydrous $MgSO_4$ and evaporated to give the title compound (293 mg) as a colorless oil.

REFERENCE EXAMPLE 5

Preparation of 5-(N-hydroxyamino)-3-phenyltridecanoic acid

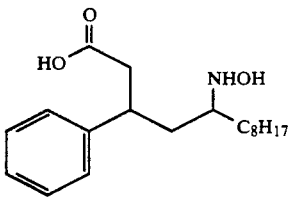

To a solution of the compound prepared in reference example 4 (190 mg) in acetic acid (2 ml) at room temperature was added sodium cyanoborohydride (57 mg). After stirring for 6 h at room temperature the reaction mixture was poured into 10 ml of $H_2O$ and extracted twice with 5 ml portions of EtOAc. The combined EtOAc extracts were dried over anhydrous $MgSO_4$, filtered and evaporated. The residue was dissolved in 30 ml of benzene and evaporated to give the title compound (127 mg) as a colorless oil.

Example 1 and 1(a)

Preparation of cis-1-hydroxy-6-octyl-4-phenylpiperidin-2-one and trans-1-hydroxy-6-octyl-4-phenylpiperidin-2-one

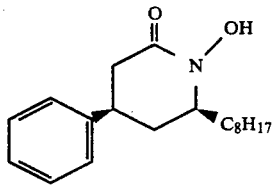

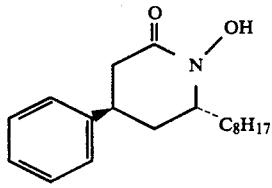

To a solution of the compound prepared in reference example 5 (127 mg) in benzene (5 ml) was added silica gel (100 mg). After refluxing for 10 h, the silica gel was filtered off. The filtrate was evaporated. The residue was purified by column chromatography on silica gel using a mixture of petroleum ether and EtOAc (3:1) to give the title compound (cis-isomer, 34 mg; trans-isomer, 52 mg) having the following physical data;

1: cis-isomer: TLC: Rf 0.41 (petroleum ether:EtOAc=3:1); NMR: δ7.35 (t, 2H), 7.27 (t, 1H), 7.22 (d, 2H), 3.85 (m, 1H), 3.05 (tt, 1H), 2.75 (dt, 1H), 2.61 (dd, 1H), 2.27 (m, 1H), 2.04 (m, 1H), 1.86 (q, 1H), 1.63 (m, 1H), 1.27 (bs, 12H) and 0.88 (t, 3H).

1(a) trans-isomer: TLC: Rf 0.29 (petroleum ether:EtOAc=3:1); NMR: δ7.35 (t, 2H), 7.27 (t, 1H), 7.23 (d, 2H), 3.75 (m, 1H), 3.26 (m, 1H), 2.77 (dd, 1H), 2.60 (dd, 1H), 2.13 (m, 3H), 1.61 (m, 1H), 1.27 (bs, 12H) and 0.88 (t, 3H)

Example 1(b)–1(cc)

By the same procedures shown in reference example 4, 5 and example 1, compounds having the physical data described in following Table II were prepared.

TABLE II

| Example No. | Structure | Name | TLC (Rf) | NMR (δ) |
|---|---|---|---|---|
| 1(b) | 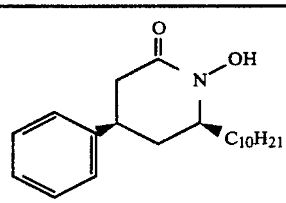 | cis-1-hydroxy-6-decyl-4-phenyl-piperidin-2-one | — | 7.36(t, 2H), 7.27(t, 1H), 7.21(d, 2H), 3.86(m, 1H), 3.06(tt, 1H), 2.75(dt, 1H), 2.61(dd, 1H), 2.29(dp, 1H), 2.03(m, 1H), 1.86(q, 1H), 1.64(m, 1H), 1.26(bs, 16H), 0.88(t, 3H) |
| 1(c) | 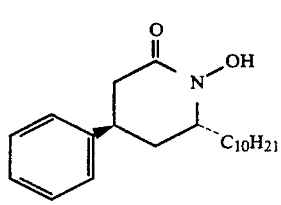 | trans-1-hydroxy-6-decyl-4-phenyl-piperidin-2-one | 0.16 (petroleum ether:EtOAc = 5:1) | 7.36(t, 2H), 7.27(t, 1H), 7.23(d, 2H), 3.76(m, 1H), 3.25(m, 1H), 2.78(dd, 1H), 2.61(dd, 1H), 2.13(m, 3H), 1.62(m, 1H), 1.27(bs, 16H), 0.88(t, 3H) |

TABLE II-continued

| Example No. | Name | TLC (Rf) | NMR (δ) |
|---|---|---|---|
| 1(d) | cis-1-hydroxy-6-dodecyl-4-phenyl-piperidine-2-one | 0.26 (petroleum ether:EtOAc = 5:1) | 7.36(t, 2H), 7.27(t, 1H), 7.23(d, 2H), 3.85((m, 1H), 3.06(tt, 1H), 2.75(dt, 1H), 2.61(dd, 1H), 2.27(dp, 1H), 2.04(m, 1H), 1.86(q, 1H), 1.63(m, 1H), 1.26(bs, 20H), 0.88(t, 3H) |
| 1(e) | trans-1-hydroxy-6-dodecyl-4-phenylpiperidin-2-one | 0.17 (petroleum ether:EtOAc = 5:1) | 7.36(t, 2H), 7.27(t, 1H), 7.22(d, 2H), 3.76(m, 1H), 3.25(m, 1H), 2.78(dd, 1H), 2.61(dd, 1H), 2.13(m, 3H), 1.62(m, 1H), 1.27(bs, 20H), 0.90(t, 3H) |
| 1(f) | cis-1-hydroxy-4-phenyl-6-tetradecyl-piperidin-2-one | 0.73 (petroleum ether:EtOAc = 1:1) | — |
| 1(g) | trans-1-hydroxy-4-phenyl-6-tetradecyl-piperidine-2-one | 0.61 (petroleum ether:EtOAc = 1:1) | — |
| 1(h) | cis-1-hydroxy-6-octadecyl-4-phenylpiperidin-2-one | 0.75 (petroleum ether:EtOAc = 1:1) | — |
| 1(i) | trans-1-hydroxy-6-octadecyl-4-phenylpiperidin-2-one | 0.63 (petroleum ether:EtOAc = 1:1) | — |
| 1(j) | cis-1-hydroxy-4-phenyl-6-(3-phenylpropyl)-piperidin-2-one | 0.36 (petroleum ether:EtOAc = 3:1) | 9.0(bs, 1H), 7.1–7.4(m, 10H), 3.88(m, 1H), 3.04(m, 1H), 2.74(m, 1H), 2.67(t, 2H), 2.58(dd, 1H), 2.23(m, 1H), 1.85(q, 1H), 1.70(t, 2H), 1.64(m, 1H) |
| 1(k) | trans-1-hydroxy-4-phenyl-6-(3-phenylpropyl)-piperidin-2-one | 0.26 (petroleum ether:EtOAc = 3:1) | 9.2(bs, 1H), 7.1–7.4(m, 10H), 3.78(m, 1H), 3.20(m, 1H), 2.76(m, 1H), 2.66(t, 2H), 2.61(dd, 1H), 2.14(m, 3H), 1.70(m, 3H) |

TABLE II-continued

| Example No. | Structure | Name | TLC (Rf) | NMR (δ) |
|---|---|---|---|---|
| 1(l) | (cis structure with phenyl, C$_7$H$_{14}$-phenyl, N-OH piperidinone) | cis-1-hydroxy-4-phenyl-6-(7-phenylheptyl)-piperidin-2-one | 0.51 (petroleum ether:EtOAc = 3:1) | — |
| 1(m) | (trans structure with phenyl, C$_7$H$_{14}$-phenyl, N-OH piperidinone) | trans-1-hydroxy-4-phenyl-6-(7-phenylheptyl)-piperidin-2-one | 0.30 (petroleum ether:EtOAc = 3:1) | — |
| 1(n) | (cis structure with 1-naphthyl, C$_8$H$_{17}$, N-OH piperidinone) | cis-1-hydroxy-4-(1-naphthyl)-6-octylpiperidin-2-one | 0.57 (petroleum ether:EtOAc = 1:1) | 9.0(bs, 1H), 8.05(d, 1H), 7.91(d, 1H), 7.08(d, 1H), 7.57(t, 1H), 7.55(t, 1H), 7.49(t, 1H), 7.37(d, 1H), 4.01(m, 1H), 3.89(tt, 1H), 2.93(dt, 1H), 2.73(dd, 1H), 2.43(m, 1H), 2.08(m, 1H), 2.02(q, 1H), 1.68(m, 1H), 1.28(bs, 12H), 0.89(t, 3H) |
| 1(o) | (trans structure with 1-naphthyl, C$_8$H$_{17}$, N-OH piperidinone) | trans-1-hydroxy-4-(1-naphthyl)-6-octylpiperidin-2-one | 0.46 (petroleum ether:EtOAc = 1:1) | 9.6(bs, 1H), 8.07(d, 1H), 7.92(d, 1H), 7.80(d, 1H), 7.56(m, 2H), 7.49(t, 1H), 7.34(d, 1H), 4.09(m, 1H), 3.80(m, 1H), 2.99(dd, 1H), 2.75(dd, 1H), 2.23(m, 3H), 1.77(m, 1H), 1.29(bs, 12H), 0.89(t, 3H) |
| 1(p) | (cis structure with 2-naphthyl, C$_8$H$_{17}$, N-OH piperidinone) | cis-1-hydroxy-4-(2-naphthyl)-6-octylpiperidin-2-one | 0.51 (petroleum ether:EtOAc = 1:1) | 8.9(bs, 1H), 7.83(t, 3H), 7.64(S, 1H), 7.49(m, 2H), 7.34(dd, 1H), 3.90(m, 1H) 3.21(tt, 1H), 2.84(dt, 1H), 2.72(dd, 1H), 2.35(m, 1H), 2.07(m, 1H), 1.96(q, 1H), 1.66(m, 1H), 1.28(bs, 12H), 0.89(t, 3H) |
| 1(q) | (trans structure with 2-naphthyl, C$_8$H$_{17}$, N-OH piperidinone) | trans-1-hydroxy-4-(2-naphthyl)-6-octylpiperidin-2-one | 0.37 (petroleum ether:EtOAc = 1:1) | 9.40(bs, 1H), 7.83(t, 3H), 7.65(s, 1H), 7.50(m, 2H), 7.33(d, 1H), 3.79(m, 1H), 3.39(m, 1H), 2.88(dd, 1H), 2.73(dd, 1H), 2.20(m, 3H), 1.68(m, 1H), 1.30(bs, 12H), 0.91(t, 3H) |
| 1(r) | (pyrrolidinone with 3-phenylpropyl and C$_8$H$_{17}$, N-OH) | 1-hydroxy-5-octyl-3-(3-phenyl propyl)pyrrolidin-2-one (mixture of cis and trans isomers) | — | 7.27(2H), 7.18(3H), 3.70 & 3.63(1H), 2.62(2H), 2.42(1H), 2.18 & 2.02(1H), 1.97–1.54(5H), 1.49–0.98(m), 0.89(m, 3H) |
| 1(s) | (pyrrolidinone with C$_{12}$H$_{25}$, phenyl, N-OH) | 1-hydroxy-4-phenyl-3-dodecyl-pyrrolidin-2-one (mixture of cis and trans isomers) | 0.36 (CH$_2$Cl$_2$: MeOH = 95:5) | 7.40–7.14(5H), 4.06(dd), 4.00(t), 3.81(dd), 3.67(t) 3.63(dt), 3.23(q), 2.79(m), 2.66(m), 1.58(m), 1.78(m), 1.40–0.96(brs), 0.91(m, 9H) |

TABLE II-continued

| Example No. | Structure | Name | TLC (Rf) | NMR (δ) |
|---|---|---|---|---|
| 1(t) | 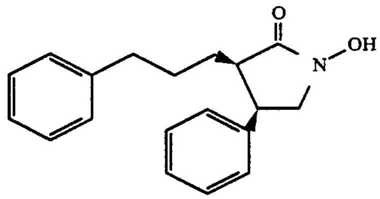 | cis-1-hydroxy-4-phenyl-3-(3-phenylpropyl)-pyrrolidin-2-one | 0.33 (CH₂Cl₂: MeOH = 95:5) | 7.40-7.12(m, 8H), 7.05(dt, 2H), 3.95(t, 1H), 3.68(dd, 1H), 2.65(m, 2H), 1.82(m, 1H), 1.68(m, 3H) |
| 1(u) | 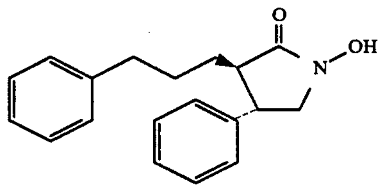 | trans-1-hydroxy-4-phenyl-3-(3-phenylpropyl)-pyrrolidin-2-one | 0.33 (CH₂Cl₂: MeOH = 95:5) | 7.47-7.00(m, 8H), 7.00(d, 2H), 4.03(dd, 1H), 3.77(dd, 1H), 3.59(dt, 1H), 2.77(dt, 1H), 2.47(ddd, 1H), 2.35(ddd, 1H), 1.75-1.45(m, 3H), 1.12(m, 1H) |
| 1(v) | 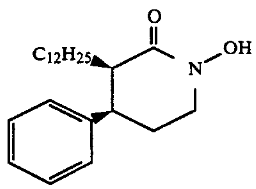 | cis-1-hydroxy-4-phenyl-3-dodecylpiperidin-2-one | 0.36 (CH₂Cl₂: MeOH = 95:5) | 7.5-7.4(3H), 7.30(d, 2H), 3.69(t, 1H), 3.38(m, 1H), 2.74(m, 1H), 2.37-2.20(2H), 1.68(m, 1H), 1.20-0.90(m), 0.88(m, 3H) |
| 1(w) | 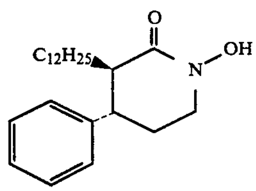 | trans-1-hydroxy-4-phenyl-3-dodecylpiperidin-2-one | — | 7.41-7.06(5H), 3.72(m, 2H), 2.97(m, 1H), 2.75(m, 1H), 2.16(m, 2H), 1.74(m, 1H), 1.56-0.96(m), 0.88(m, 3H) |
| 1(x) | 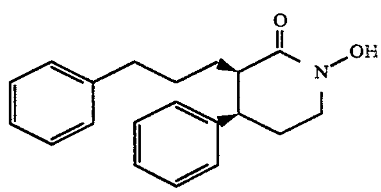 | cis-1-hydroxy-4-phenyl-3-(3-phenylpropyl)-piperidin-2-one | — | 7.39-7.07(8H), 7.01(dt, 1H), 3.67(t, 1H), 3.37(dt, 1H), 2.76(q, 1H), 2.45(t, 2H), 1.82-1.22(4H) |
| 1(y) | 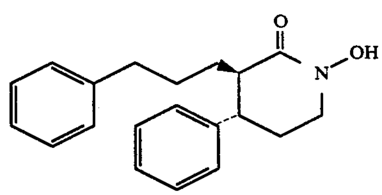 | trans-1-hydroxy-4-phenyl-3-(3-phenylpropyl)-piperidin-2-one | — | 7.38-7.07(10H), 3.70(m, 2H), 2.93(m, 1H), 2.74(m, 1H), 2.58(m, 1H), 2.46(m, 1H), 2.15(m, 1H), 1.90-1.37(4H), 1.38(m, 1H) |
| 1(z) | 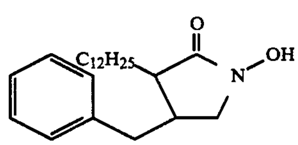 | 1-hydroxy-4-benzyl-3-dodecylpyrrolidin-2-one (mixture of cis and trans isomers) | 0.35 (CH₂Cl₂: MeOH ± 95:5) | — |
| 1(aa) | 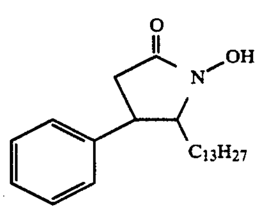 | 1-hydroxy-4-phenyl-5-tridecyl-pyrrolidin-2-one (mixture of cis and trans isomers) | 0.26 (EtOAc hexane = 1:1) | 7.40-7.24(3H), 7.17(d, 2H), 4.71(m, 1H), 3.59(m, 1H), 3.08(dd, 1H), 2.86(dd, 1H), 1.65(m, 1H), 1.50-1.00(m), 0.90(m, 3H) |

TABLE II-continued

| Example No. | Structure | Name | TLC (Rf) | NMR (δ) |
|---|---|---|---|---|
| 1(bb) | ![structure] | cis-1-hydroxy-5-heptyl-3-phenyl-pyrrolidin-2-one | 0.48 (petroleum ether: EtOAc = 6:4) | 7.43–7.22(5H), 6.32(bs, 1H), 4.66(m, 1H), 4.13(dd, 1H), 2.32(m, 2H), 1.86(m, 1H), 1.73–1.18(m), 1.89(m, 3H) |
| 1(cc) | ![structure] | trans-1-hydroxy-5-heptyl-3-phenyl-pyrrolidin-2-one | 0.43 (petroleum ether: EtOAc = 6:4) | 7.44–7.20(5H), 6.31(bs, 1H), 4.52(m, 1H), 4.08(dd, 1H), 2.65(ddd, 1H), 1.95(m, 2H), 1.80–1.17(m), 0.89(m, 3H) |

-continued

FORMULATION EXAMPLE 1

The following components were admixed in conventional method and punched out to obtain 100 tablets each containing 50 mg of active ingredient.

| | |
|---|---|
| trans-1-hydroxy-6-octyl-4-phenyl-piperidin-2-one | 5 g |
| Cellulose calcium glycolate (disintegrating agent) | 0.2 g |
| Magnesium stearate (lubricating agent) | 0.1 g |
| Microcrystalline cellulose | 4.7 g |

FORMULATION EXAMPLE 2

The following components were admixed in conventional manner.

The solution was sterilized in conventional manner, placed 2 ml portions into 5 ml ampules and freeze-dried to obtain 100 ampules each containing 20 mg of the active ingredient.

| | |
|---|---|
| trans-1-hydroxy-6-octyl-4-phenylpiperidin-2-one | 2 g |
| citric acid | 200 mg |
| distilled water | 500 ml |

What is claimed is:

1. A cyclic hydroxamic acid of the formula:

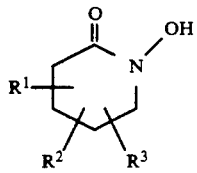

$R^1$, $R^2$ and $R^3$ each, independently, is hydrogen, C1-24 alkyl, C2-24 alkenyl or a group of the formula:

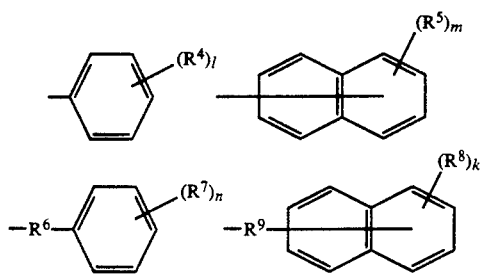

wherein $R^4$, $R^5$, $R^7$ and $R^8$ each, independently is hydrogen, C1-4 alkyl, C1-4 alkoxy, trifluoromethyl, halogen or nitro;

l is 1-3;
m is 1-3;
n is 1-3;
k is 1-3;

$R^6$ and $R^9$ each, independently is C1-24 alkylene or C2-24 alkenylene;

with the proviso that, more than one of $R^1$, $R^2$ and $R^3$ are not hydrogen at the same time; and the pharmaceutically acceptable salts thereof.

2. The compound according to claim 1, wherein one of $R^1$, $R^2$ and $R^3$ is phenyl or phenylalkyl.

3. The compound according to claim 2, which is selected from the group consisting of 1-hydroxy-6-octyl-4-phenylpiperidine-2-one, 1-hydroxy-6-decyl-4-phenylpiperidin-2-one, 1-hydroxy-6-dodecyl-4-phenyl-piperidin-2-one, 1-hydroxy-6-tetradecyl-4-phenyl-piperidin-2-one, 1-hydroxy-6-octadecyl-4-phenylpiperidin-2-one and 1-hydroxy-4-phenyl-3-dodecylpiperidin-2-one.

4. The compound according to claim 1, wherein two of $R^1$, $R^2$ and $R^3$ are phenyl or phenylalkyl.

5. The compound according to claim 4, which is selected from the group consisting of 1-hydroxy-4-phenyl-6-(3-phenylpropyl)piperidin-2-one, 1-hydroxy-4-phenyl-6-(7-phenylhepty)piperidine-2-one and 1-hydroxy-4-phenyl-3-(3-phenylpropyl)piperidin-2-one.

6. The compound according to claim 1, wherein one of $R^1$, $R^2$ and $R^3$ is naphthyl or naphthylalkyl.

7. The compound according to claim 6, which is selected from the group consisting of 1-hydroxy-4-(1-naphthyl)-6-octylpiperidin-2-one and 1-hydroxy-4-(2-naphthyl)-6-octylpiperidin-2-one.

8. The composition for the inhibition of of 12-lipoxygenase, which comprises a formulation including, as active ingredient, an effective amount of a cyclic hydroxamic acid of the formula (I) of claim 1 to inhibit the 12-lipoxygenase.

9. A method for the inhibition of of 12-lipoxygenase in buffer which comprises adding an effective amount of a cyclic hydroxamic acid of the formula (I) to the 12-lipoxygenase containing buffer so as to inhibit the 12-lipoxygenase.

* * * * *

UNITED STATES PATENT AND TRADEMARK OFFICE
CERTIFICATE OF CORRECTION

PATENT NO. : 5,234,933
DATED : August 10, 1993
INVENTOR(S) : Lawrence J. Marnett, et al It is certified that error appears in the above-indentified patent and that said Letters Patent is hereby corrected as shown below:

Column 6, line 56 "$\overrightarrow{NH_2O88H}$" should be --$\overrightarrow{NH_2OH}$--.

Column 9, line 61, "5/8" should be --1/3--.

Column 16, Table II NMR column for 1(n), "7.91(d, 1H), 7.08(d, 1H)" should read --7.91(d, 1H), 7.80(d, 1H)--.

Column 18, Table II TLC column for 1(z), "MeOH±" should read --MeOH = --.

Signed and Sealed this

Twenty-second Day of March, 1994

BRUCE LEHMAN

*Attest:*

*Attesting Officer*          *Commissioner of Patents and Trademarks*